(12) United States Patent
Zhang et al.

(10) Patent No.: US 12,285,531 B2
(45) Date of Patent: Apr. 29, 2025

(54) WOUND COVERING AND PREPARATION METHOD THEREOF

(71) Applicant: Zhende Medical Co., Ltd., Shaoxing (CN)

(72) Inventors: Rui Zhang, Shaoxing (CN); Jianguo Lu, Shaoxing (CN); Luping Zhao, Shaoxing (CN); Yu Gong, Shaoxing (CN)

(73) Assignee: Zhende Medical Co., Ltd., Shaoxing (CN)

( * ) Notice: Subject to any disclaimer, the term of this patent is extended or adjusted under 35 U.S.C. 154(b) by 313 days.

(21) Appl. No.: 17/822,210

(22) Filed: Aug. 25, 2022

(65) Prior Publication Data
US 2022/0401615 A1    Dec. 22, 2022

Related U.S. Application Data

(63) Continuation of application No. PCT/CN2020/119571, filed on Sep. 30, 2020.

(30) Foreign Application Priority Data

Aug. 27, 2020  (CN) .......................... 202010877367.7

(51) Int. Cl.
| | | |
|---|---|---|
| *A61L 15/22* | (2006.01) | |
| *A61L 15/32* | (2006.01) | |
| *A61L 15/42* | (2006.01) | |
| *A61L 15/44* | (2006.01) | |
| *A61L 15/46* | (2006.01) | |
| *A61L 15/58* | (2006.01) | |
| *A61L 26/00* | (2006.01) | |

(52) U.S. Cl.
CPC ............ *A61L 15/44* (2013.01); *A61L 15/325* (2013.01); *A61L 15/58* (2013.01); *A61L 2300/214* (2013.01); *A61L 2300/216* (2013.01); *A61L 2300/412* (2013.01)

(58) Field of Classification Search
CPC ................ A61F 13/00; A61F 13/00008; A61F 13/0266; A61F 13/023; A61F 2013/00246; A61F 2013/00259; A61F 2013/00582; A61K 38/00; A61L 31/16; A61L 26/0033; A61L 2300/00; A61L 15/225; A61L 15/32; A61L 15/325; A61L 15/42; A61L 15/44; A61L 15/46

See application file for complete search history.

(56) References Cited

U.S. PATENT DOCUMENTS

2010/0137902 A1 * 6/2010 Lee ...................... A61L 31/041
                                                            606/213

FOREIGN PATENT DOCUMENTS

| CN | 103520766 A | * | 1/2014 | |
|---|---|---|---|---|
| CN | 103638554 A | | 3/2014 | |
| CN | 106310384 A | | 1/2017 | |
| CN | 107485728 A | | 12/2017 | |
| CN | 109985271 A | | 7/2019 | |
| CN | 110974810 A | * | 4/2020 | ............. A61K 31/14 |
| CN | 111346256 A | | 6/2020 | |
| CN | 111995777 A | * | 11/2020 | ............. C08J 3/075 |
| WO | WO-2009037571 A2 | | 3/2009 | |
| WO | WO-2017101020 A1 | | 6/2017 | |
| WO | WO-2017101027 A1 | | 6/2017 | |
| WO | WO-2018093161 A1 | | 5/2018 | |
| WO | WO-2022041401 A1 | | 3/2022 | |

OTHER PUBLICATIONS

Xu, Apr. 10, 2020, Film-forming wound protecting liquid as well as preparation method and application thereof.*
Gao, Jan. 22, 2014, Mussel mucoprotein liquid product as well as preparation method and application thereof.*
Pubchem, Sep. 15, 2015.*
Bao, Nov. 27, 2020, Preparation method of PEGDA-mussel adhesive protein-collagen composite hydrogel with strong adhesion and high mechanical strength.*
"International Application No. PCT/CN2020/119571, International Search Report and Written Opinion mailed May 27, 2021", (May 27, 2021), 12 pgs.
"Chinese Application No. 202010877367.7, Chinese Search Report dated Mar. 24, 2021", (Mar. 24, 2021), 2 pgs.
"Chinese Application No. 202010877367.7, First Office Action dated Mar. 24, 2021", (Mar. 24, 2021), 9 pgs.

* cited by examiner

*Primary Examiner* — Alireza Nia
*Assistant Examiner* — Andrew Jun-Wai Mok
(74) *Attorney, Agent, or Firm* — Schwegman Lundberg & Woessner, P.A.

(57) ABSTRACT

The present invention relates to a wound covering with prominent biocompatible and accelerated wound-healing and its preparation method thereof. The wound covering comprises a film prepared from collagen and Dopa-containing protein—mussel adhesive protein, which is immobilized on collagen by chemical cross-linking, thus enhances the stability of protein structure and maintains the activity of collagen and mussel adhesive protein. The wound covering has excellent mechanical strength and can be trimmed into any shape; it accelerates tissue epithelisation and promotes wound healing with good biocompatibility, non-adhesive to the wound and no further wound damages.

4 Claims, No Drawings

WOUND COVERING AND PREPARATION METHOD THEREOF

CROSS-REFERENCE TO RELATED APPLICATIONS

This application is a continuation of International Application No. PCT/CN2020/119571 filed 30 Sep. 2020, which claims the benefit of priority to Chinese Application No. 202010877367.7, filed 27 Aug. 2020, the benefit of priority of each of which is claimed herein and which applications are hereby incorporated by reference herein in their entirety.

TECHNICAL FIELD

The invention relates to a medical material, in particular to a wound covering with good biocompatibility and accelerated healing and a preparation method thereof.

BACKGROUND

The main functions of the medical dressing are to cover and protect damaged skin, and at the same time provide an environment for promoting wound healing. The medical dressing should be non-irritant to the human body and should not cause toxicity and pathological changes.

The prior art covering donor area or burn wound mainly adopts vaseline gauze, hydrocolloid dressing and other dressing which does not have biological activity. However, the defect is that: (1) it consumes a long time for wound healing; and (2) the wound surface needs to be subjected to multiple times of dressing change during treatment, so that granulation tissue bleeding and pain to a patient can be caused.

SUMMARY OF THE INVENTION

The object of the present invention is to solve the problems that an existing dressing with no biological activity takes long time for wound healing, and subjects to multiple times of dressing change during treatment that causes granulation tissue bleeding and pain to a patient; and a wound covering with prominent mechanical strength and biocompatibility is provided to promote wound healing.

Another object of the present invention is to provide a method for preparing the wound covering.

In order to achieve above purposes, the technical solution of present invention is as follows:

A wound covering comprising a film, wherein the film is prepared from a biocompatible and high-mechanical-strength carrier and a Dopa-containing protein; wherein the carrier is collagen, and the Dopa-containing protein is mussel adhesive protein.

The mussel adhesive protein (MAP) contains 20% lysine, which is positively charged so that MAP may binds to negatively charged human tissue cells through electrostatic adsorption, thereby promoting cell adhesion, accelerating wound repair and promoting healing. MAP also contains 10% Dopa, which consumes oxygen in the environment and has a strong ability to trap free radicals such as reactive oxygen species, enabling MAP as a strong antioxidant and free radical scavenger. Mussel mucin is the only known protein with a high content of Dopa groups, which can continue to exert anti-inflammatory, antioxidant and pro-repair effects locally under positive and negative charge physisorption.

Collagen, the main component of the extracellular matrix, can be made into a film carrier with good biocompatibility and excellent mechanical strength, but collagen films alone lack the ability to promote cell growth.

The present invention combines collagen and mussel adhesive protein and produces a dry film by half-lyophilisation at low temperature; then immobilize the mussel adhesive protein to collagen with chemical cross-link reaction; rinse to remove residual crosslink agent and store in the preservation solution.

When used for wound repair, the wound covering of the present invention has good moisturizing and hygroscopic properties, which can preserve wound exudate effectively while not forming any effusion; it will not adhere to wound exudate to form a scab or cause pain when during dressing changes, nor result new tissue damage. It has better antibacterial properties to prevent would infection and prominent biocompatibility, solving the problems of prior art that antibiotics intake would damage the gastrointestinal tract, liver and kidneys, and flushing the wound with saline water would trigger pain and new wounds during dressing changes.

Preferably, the mass ratio of collagen to mussel adhesive protein is 3:1~20:1.

More preferably, the film is made of collagen and mussel adhesive protein through chemical cross-linking, and the dry weight of the unit area of the film is 1-5 mg/cm$^2$.

More preferably, the wound covering further comprises a preservation solution, the preservation solution is a mixed solution containing glycerol and sodium hydrogen phosphate.

The present invention further provides a preparation method of the wound covering comprising the following steps:

(a) preparing for a film containing collagen and mussel adhesive protein:
  (i) dissolving mussel adhesive protein in a glacial acetic acid solution, configuring a mussel adhesive protein preservation solution with a concentration of 0.4%;
  (ii) taking $\frac{1}{20}$-$\frac{1}{4}$ of the mussel adhesive protein preservation solution of the step (i), and adding collagen to dissolve to obtain a mixed solution;
  (iii) transferring the mixed solution of step (ii) into a stainless steel plate with a solution height of 2.4-12.5 mm; and lyophilizing for 7-15 hours at a temperature of −10° C. and under a vacuum degree of 10-50 Pa; then quickly increasing the temperature of the plate to 10° C. and the vacuum degree to 300-500 Pa and drying for 3 hours; and finally adjusting the temperature to 20° C. and the vacuum degree 10-50 Pa and drying for 8-14 hours to for a dried film;
  (iv) transferring the dried film of the step (iii) into a crosslink agent, cross-linking for 2 hours, taking out and rinsing several times for later use;

(b) preparing for a preservation solution: dissolving glycerol and sodium dihydrogen phosphate in purified water, adjusting the pH to 4-7 at a constant volume of 1 L;

(c) finishing producing: placing the film containing collagen and mussel adhesive protein of the step (a) in a packet, adding the preservation solution of the step (b), sealing and stored in an aluminum foil bag.

Step (iii) of present invention starts with lyophilisation at −10° C., where approximately 40% of the water still contained in the sample is in the form of ice crystals due to the system temperature being below 0° C. and the low system pressure (10-50 pa). A further increase in system temperature above 0° C. (10° C.) and an appropriate increase in system pressure to 300-500 Pa allows the ice crystals to change to a liquid state, thus allowing the carrier to collapse to form a uniform gel-like film at low temperatures.

The purpose of increasing the temperature of the plate to 20° C. and reducing the vacuum degree back to 10-50 Pa is to further remove the residual moisture from the sample so that the moisture in the sample is reduced to less than 10% to form a dry, strong film.

Preferably, the mixed solution in the step (ii) comprises collagen at a concentration of 0.3-0.4% and mussel adhesive protein at a concentration of 0.02-0.1%.

Preferably, in the step (b), dissolving parts by weight of glycerol and 10 parts by weight of sodium dihydrogen phosphate in 900 mL purified water.

Preferably, in the step (c), the adding amount of the preservation solution is 2-5 mL/cm$^2$.

Preferably, the crosslink agent used in the step (iv) is selected from the group consisting of formaldehyde, glutaraldehyde, kynepin and carbodiimide.

Beneficial effects of present invention: The present invention combines collagen and mussel adhesive protein, forms a dry film by half-lyophilisation at low temperature, then immobilizes the mussel adhesive protein to collagen with chemical cross-link reaction; rinses to remove residual crosslink agent and stores in the preservation solution, which enhances the stability of the protein structure and maintains the activity of the collagen and mussel adhesive protein. The collagen base has excellent mechanical strength and can be trimmed to any shape; it accelerates tissue epithelisation and promotes wound healing with good biocompatibility, non-adhesive to the wound and no further wound damages.

DETAILED DESCRIPTION OF THE INVENTION

The invention is further illustrated in detail below by means of embodiments, but it is understood by those skilled in the art that the embodiments of the invention are not a limitation on the scope of protection of the invention and that any improvements and variations made on the basis of the invention are within the scope of protection of the invention. All materials in the present invention can be acquired from the market.

Embodiment 1

This embodiment provides a wound covering and its preparation method comprising the following steps:
(a) preparing for a film containing collagen and mussel adhesive protein
  (i) dissolving mussel adhesive protein in 0.0001 mol/L glacial acetic acid solution, configuring a mussel adhesive protein preservation solution with a concentration of 0.4%;
  (ii) taking 5 parts of the mussel adhesive protein preservation solution of the step (i) and diluting to 20 parts with water; and adding collagen to dissolve to obtain a mixed solution with sufficient stirring to give the collagen concentration of 0.5% and the mussel adhesive protein concentration of 0.1%;
  (iii) transferring the mixed solution of step (ii) into a 30*30 cm stainless steel plate with a solution height of 5 mm; and lyophilizing for 10 hours at a temperature of −10° C. and under a vacuum degree of 10-50 Pa, where approximately 40% of the water still contained in the sample is in the form of ice crystals due to the temperature and pressure of the system. Then quickly increasing the temperature of the plate to 10° C. and the vacuum degree to 300-500 Pa and drying for 3 hours so that the ice crystals become liquid and the carrier collapses at low temperatures to form a uniform gel-like film. Then finally adjusting the temperature to 20° C. and the vacuum degree 10-50 Pa and drying for 10 hours, thus further removes the residual moisture from the sample to less than 10% to form a dry and strong film. Then slitting of the collagen-MAP film into the required size and shape by passing it through a slitting die;
  (iv) transferring the dried collagen-MAP film into a 0.1% formaldehyde solution with adding amount 5 mL/cm$^2$ of the film and cross-linking for 2 hours, taking out and rinsing 8 times for later use;
(b) preparing for a preservation solution is dissolving 10 g glycerol and 31.2 g sodium dihydrogen phosphate in purified water of 900 mL, adjusting the pH to 5.0 by using sodium hydroxide solution, and adding water at a constant volume to 1 L;
(c) finishing producing placing the rinsed collagen-MAP film in a packet, adding the preservation solution at a ratio of 2 mL/cm$^2$, sealing and stored in an aluminum foil bag.

Embodiment 2

This embodiment provides a wound covering and its preparation method comprising the following steps:
(a) preparing for a film containing collagen and mussel adhesive protein
  (i) dissolving mussel adhesive protein in 0.0001 mol/L glacial acetic acid solution, configuring a mussel adhesive protein preservation solution with a concentration of 0.4%;
  (ii) taking 5 parts of the mussel adhesive protein preservation solution of the step (i) and diluting to 20 parts with water; and adding collagen to dissolve to obtain a mixed solution with sufficient stirring to give the collagen concentration of 0.3% and the mussel adhesive protein concentration of 0.1%;
  (iii) transferring the mixed solution into a 30*30 cm stainless steel plate with a solution height of 12.5 mm; and lyophilizing for 15 hours at a temperature of −10° C. and under a vacuum degree of 10-50 Pa; then quickly increasing the temperature of the plate to 10° C. and the vacuum degree to 300-500 Pa and drying for 3 hours; adjusting the temperature to 20° C. and the vacuum degree 10-50 Pa and drying for 14 hours, Then slitting of the collagen-MAP film into the required size and shape by passing it through a slitting die.
  (iv) transferring the dried collagen-MAP film into a 0.1% formaldehyde solution with adding amount 5 mL/cm$^2$ of the film and cross-linking for 2 hours, taking out and rinsing 8 times;
(b) preparing for a preservation solution dissolving 10 g glycerol and 31.2 g sodium dihydrogen phosphate in purified water of 900 mL, adjusting the pH to 5.0 by using sodium hydroxide solution, and adding water at a constant volume to 1 L;

(c) finishing producing placing the rinsed collagen-MAP film in a packet, adding the preservation solution at a ratio of 2 mL/cm$^2$, sealing and stored in an aluminum foil bag.

Embodiment 3

This embodiment provides a wound covering and its preparation method comprising the following steps:
(a) preparing for a film containing collagen and mussel adhesive protein
  (i) dissolving mussel adhesive protein in 0.0001 mol/L glacial acetic acid solution, configuring a mussel adhesive protein preservation solution with a concentration of 0.4%;
  (ii) taking 1 parts of the mussel adhesive protein preservation solution of the step (i) and diluting to 20 parts with water; and adding collagen to dissolve to obtain a mixed solution with sufficient stirring to give the collagen concentration of 0.4% and the mussel adhesive protein is concentration of 0.02%;
  (iii) transferring the mixed solution into a 30*30 cm stainless steel plate with a solution height of 2.4 mm; and lyophilizing for 7 hours at a temperature of −10° C. and under a vacuum degree of 10-50 Pa; then quickly increasing the temperature of the plate to 10° C. and the vacuum degree to 300-500 Pa and drying for 3 hours; adjusting the temperature to 20° C. and the vacuum degree 10-50 Pa and drying for 8 hours, Then slitting of the collagen-MAP film into the required size and shape by passing it through a slitting die.
  (iv) transferring the dried collagen-MAP film into a 0.1% formaldehyde solution with adding amount 5 mL/cm$^2$ of the film and cross-linking for 2 hours, taking out and rinsing 8 times;
(b) preparing for a preservation solution dissolving 10 g glycerol and 31.2 g sodium dihydrogen phosphate in purified water of 900 mL, adjusting the pH to 5.0 by using sodium hydroxide solution, and adding water at a constant volume to 1 L;
(c) finishing producing
placing the rinsed collagen-MAP film in a packet, adding the preservation solution at a ratio of 2 mL/cm$^2$, sealing and stored in an aluminum foil bag.

The results of the tests carried out on the wound covering prepared in Embodiments 1-3 are shown in Table 1.

TABLE 1

| | Test Result | | |
|---|---|---|---|
| | Embodiment 1 | Embodiment 2 | Embodiment 3 |
| Sensory Evaluation | Flexible and transparent film | Flexible and transparent film | Flexible and transparent film |
| Dry Weights | 3 mg/cm$^2$ | 5 mg/cm$^2$ | 1 mg/cm$^2$ |
| Tensile Strength | No breakage of the sample (1 cm wide) hung with a 100 g weight | No breakage of the sample (1 cm wide) hung with a 150 g weight | No breakage of the sample (1 cm wide) hung with a 50 g weight |

As shown in Table 1, the present invention mixes collagen and mussel adhesive protein, makes a dry film by half-lyophilisation at low temperature, then immobilize mussel mucin on collagen by chemical cross-linking, rinses to remove residual crosslink agent and stores in preservation solution, which enhances the stability of protein structure and maintains the activity of collagen and mussel adhesive protein, the collagen substrate has excellent mechanical strength and can be trimmed into any shape; it accelerates tissue epithelisation and promotes wound healing with good biocompatibility, non-adhesive to the wound and no further wound damages.

The above schematically describes the present invention and its embodiments, the description is not limiting, and what is shown in the attached drawings is only one of the embodiments of the present invention, and the actual structure is not limited to it. Therefore, if a person of ordinary skill in the art is inspired by it and designs, without departing from the creative purpose of the invention, structural ways and embodiments similar to this technical solution without inventiveness, they shall fall within the scope of protection of the present invention.

What is claimed is:

1. A preparation method of a wound covering comprising a film, wherein the film is prepared from a biocompatible and high-mechanical-strength carrier and a Dopa-containing protein, wherein the carrier is collagen, and the Dopa-containing protein is mussel adhesive protein, comprising the following steps:
(a) preparing for the film containing collagen and mussel adhesive protein:
  (i) dissolving mussel adhesive protein in a glacial acetic acid solution, configuring a mussel adhesive protein preservation solution with a concentration of 0.4%;
  (ii) taking 1/20~1/4 of the mussel adhesive protein preservation solution of the step (i), and adding collagen to dissolve to obtain a mixed solution;
  (iii) transferring the mixed solution of step (ii) into a stainless steel plate with a solution height of 2.4-12.5 mm; and
  lyophilizing for 7-15 hours at a temperature of −10° C. and under a vacuum degree of 10-50 Pa; then quickly increasing the temperature of the plate to 10° C. and the vacuum degree to 300-500 Pa and drying for 3 hours; and finally adjusting the temperature to 20° C. and the vacuum degree 10-50 Pa and drying for 8-14 hours to for a dried film;
  (iv) transferring the dried film of the step (iii) into a crosslink agent, cross-linking for 2 hours, taking out and rinsing several times for later use;
(b) preparing for a preservation solution: dissolving glycerol and sodium dihydrogen phosphate in purified water, adjusting the pH to 4-7 at a constant volume of 1 L;
(c) finishing producing: placing the film containing collagen and mussel adhesive protein of the step (a) in a packet, adding the preservation solution of the step (b), sealing and stored in an aluminum foil bag;
wherein the mixed solution in the step (ii) comprises collagen at a concentration of 0.3-0.4% and mussel adhesive protein at a concentration of 0.02-0.1%;
wherein in the step (b), dissolving parts by weight of glycerol and 10 parts by weight of sodium dihydrogen phosphate in 900 mL purified water;
wherein in the step (c), the adding amount of the preservation solution is 2-5 mL/cm$^2$;
wherein the crosslink agent used in the step (iv) is selected from a group consisting of formaldehyde, glutaraldehyde, kynepin and carbodiimide.

2. The preparation method according to claim 1, wherein a mass ratio of collagen to mussel adhesive protein is 3:1~20:1.

3. The preparation method according to claim 2, wherein the film is made of collagen and mussel adhesive protein through chemical cross-linking.

4. The preparation method according to claim 3, wherein a dry weight of a unit area of the film is 1-5 mg/cm$^2$.

* * * * *